(12) United States Patent
Bashan et al.

(10) Patent No.: US 11,883,377 B1
(45) Date of Patent: *Jan. 30, 2024

(54) ALGAL BOTANICAL EXTRACTS RICH IN EICOSAPENTAENOIC ACID AS TRI/DI-GLYCERIDE CONJUGATE

(71) Applicant: Vaxa Technologies Ltd., Rosh Pinna (IL)

(72) Inventors: Ohad Bashan, Sde Varburg (IL); Isaac Berzin, Jerusalem (IL)

(73) Assignee: VAXA TECHNOLOGIES LTD, Rosh Pina (IL)

( * ) Notice: Subject to any disclaimer, the term of this patent is extended or adjusted under 35 U.S.C. 154(b) by 2 days.

This patent is subject to a terminal disclaimer.

(21) Appl. No.: 17/994,014

(22) Filed: Nov. 25, 2022

Related U.S. Application Data

(63) Continuation-in-part of application No. 17/950,391, filed on Sep. 22, 2022.

(51) Int. Cl.
| | |
|---|---|
| *A61K 31/202* | (2006.01) |
| *A61K 31/7028* | (2006.01) |
| *A61K 31/683* | (2006.01) |
| *A23L 33/12* | (2016.01) |
| *A61K 36/02* | (2006.01) |

(52) U.S. Cl.
CPC ............ *A61K 31/202* (2013.01); *A23L 33/12* (2016.08); *A61K 31/683* (2013.01); *A61K 31/7028* (2013.01); *A61K 36/02* (2013.01); *A23V 2002/00* (2013.01); *A61K 2236/333* (2013.01)

(58) Field of Classification Search
None
See application file for complete search history.

(56) References Cited

U.S. PATENT DOCUMENTS

| | | |
|---|---|---|
| 9,629,820 B2 | 4/2017 | Waibel et al. |
| 10,039,734 B2 | 8/2018 | Waibel et al. |
| 10,123,986 B2 | 11/2018 | Waibel et al. |
| 2014/0179781 A1 | 6/2014 | Waibel et al. |

FOREIGN PATENT DOCUMENTS

| | | | | |
|---|---|---|---|---|
| JP | H09252761 A | * | 9/1997 | ............ C12M 1/00 |
| WO | WO 2018/134818 | | 7/2018 | |
| WO | WO 2018/134819 | | 7/2018 | |
| WO | WO 2018/134820 | | 7/2018 | |
| WO | WO 2018/154565 | | 8/2018 | |
| WO | WO-2019201478 A1 | * | 10/2019 | ............ A23D 9/02 |
| WO | WO 2020/240551 | | 3/2020 | |

OTHER PUBLICATIONS

Matthew J. Scholz et al. 'Ultrastructure and Composition of the Nannochloropsis gaditana Cell Wall'; ASM Journals Eukaryotic Cell, vol. 13, No. 11, pp. 1450-1464; Published Oct. 29, 2014.

Mariane Audo et al. 'Relationship between microalgae lipid extracts composition and rheological properties'; 2nd International Symposium on Asphalt Pavements et Environnement, Transportation Research Board, of the National Academies, Jan. 2012, France.

Tom Bernaerts. 'The role of structural Biopolymers in the functionalization of microalgae for food processing: Potential as structuring agent and implications for nutrient bioaccessibility'; KU Leuven; Laboratory of Food Technology, PhD Thesis, Published May 2019.

Martin Rossmeisl et al. 'Melabolic Effects of n-3 PUFA as Phospholipids Are Superior to Triglycerides in Mice Fed a High-Fat Diet: Possible Role of Endocannabinoids'; (Plos one); vol. 7, Issue 6; Jun. 11, 2012.

Stine M. Ulven et al. 'Metabolic Effects of Krill Oil are Essentially Similar to Those of Fish Oil but at Lower Dose of EPA and DHA, in Healthy Volunteers'; Lipids, 46(1), pp. 37-46.; Nov. 2, 2010.

Lena Burri et al. 'Marine Omega-3 Phospholipids: Metabolism and Biological Activities'; Int. J. Mol. Sci., 2012, vol. 13, No. 11, pp. 15401-1541; Special Issue Phospholipids: Molecular Sciences 2012; Nov. 21, 2012.

Lena Burri et al.'Fingerprinting Krill Oil by 31P, 1H and 13C NMR Spectroscopies'; Journal of the American Oil Chemists' Society, vol. 93, No. 8, pp. 1037-1049.; Apr. 30, 2016.

Jan Philipp Schuchardt et al. 'Incorporation of EPA and DHA into plasma phospholipids in response to different omega-3 fatty acid formulations'—a comparative bioavailability study of fish oil vs. krill oil; BMC Part of Springer Nature; Lipids in Health Disease; vol. 10, No. 1; pp. 1-7; Aug. 22, 2011.

Larry D. Lawson et al.'Human Absorption of Fish Oil Fatty Acids as Triacylgycerols, Free acids, or Ethyl Esters'; Biochemical and Biophysical Research Communications; vol. 152, Issue 1; pp. 328-335, Apr. 15, 1988.

Vanu R. Ramprasath et al.; Enhanced incease of omega-3 index in healthy individuals with response to 4-week n-3 fatty acid supplementation from krill oil versus fish oil; BMC Part of Springer Nature; Lipids in Health Disease; vol. 12, No. 1; pp. 1-11; Dec. 5, 2013.

Elina Zailer; 'Holistic Control of Fats and Oils by NMR Spectroscopy'; Encyclopedia of Food Chemistry, 2019, pp. 168-181; 2019; Spectral Service AG, Cologne, Germany; © 2019 Elsevier Inc.

Elina Zailer; 'Holistic Control of Fats and Oils by NMR Spectroscopy'; Encyclopedia of Food Chemistry, 2019, pp. 168-181; 2019; Spectral Service AG, Cologne, Germany; © 2019 Elsevier Inc.

* cited by examiner

*Primary Examiner* — Dale R Miller
(74) *Attorney, Agent, or Firm* — PEARL COHEN ZEDEK LATZER BARATZ LLP

(57) ABSTRACT

Botanical extracts are provided, which comprise ethanol extracts of *Nannochloropsis* algae having between 1 wt % and 50 wt % polar lipids and between 45 wt % and 60 wt % fatty acids, wherein the fatty acids comprise more than 10 wt % of eicosapentaenoic acid (EPA) as triglyceride conjugates and/or diglyceride conjugates, and less than 15 wt % EPA as free fatty acids. EPA level may reach up to 90 wt %, and the botanical extract may be fluid at room temperature. Growth conditions are configured, adjusted and monitored to promote EPA formation in the cell vacuoles, resulting in a high proportion of EPA as tri/di-glyceride conjugates, as well as in a high concentration of Ω-3 fatty acids, which merely requires gentle extraction procedures to reach the final products, thereby maintaining the biochemical of the compounds without excessive modifications.

12 Claims, 1 Drawing Sheet

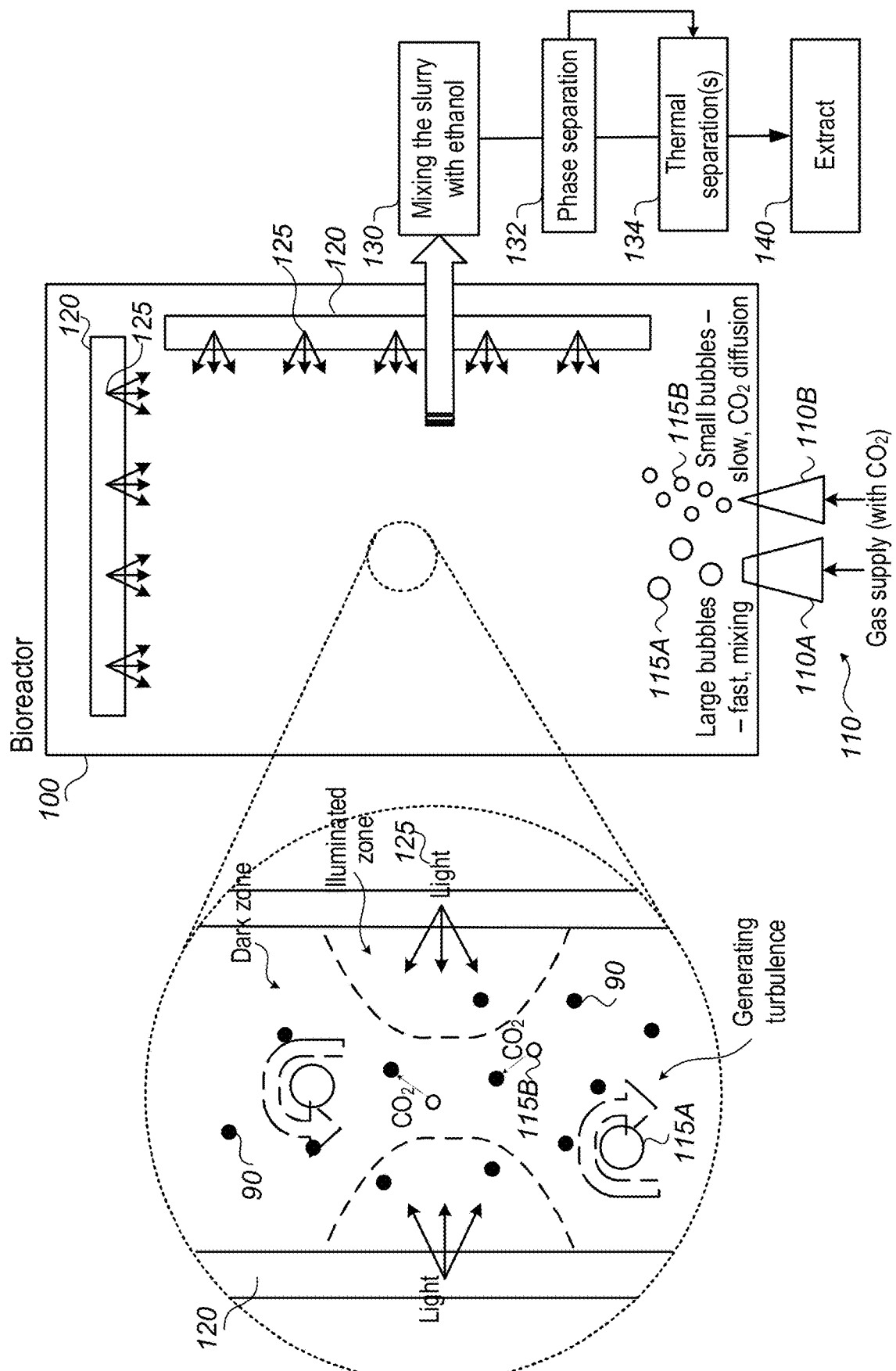

ALGAL BOTANICAL EXTRACTS RICH IN EICOSAPENTAENOIC ACID AS TRI/DI-GLYCERIDE CONJUGATE

CROSS REFERENCE TO RELATED APPLICATIONS

This application is a Continuation-In-Part of, and claims priority from U.S. application Ser. No. 17/950,391, filed on Sep. 22, 2022, which is incorporated herein by reference in its entirety.

BACKGROUND OF THE INVENTION

1. Technical Field

The present invention relates to the field of food and supplements rich in Ω3-fatty acids and, more particularly, to algal botanical extracts rich in EPA as triglyceride conjugates and/or diglyceride conjugates.

2. Discussion of Related Art

U.S. Pat. Nos. 9,629,820, 10,123,986 and 10,039,734, and U.S. Patent Application Publication No. 20140179781, which are incorporated herein by reference in their entirety, disclose eicosapentaenoic acid (EPA) compositions, as well as products and use indications therefor, which comprise from about 15 wt % to about 90 wt % EPA and about 10 wt % to about 70 wt % polar lipids, wherein the polar lipids comprise phospholipid conjugates and glycolipid conjugates; about 3 wt % to about 50 wt % of the EPA in the composition is a phospholipid conjugate; about 5 wt % to about 50 wt % of the EPA in the composition is a glycolipid conjugate; about 0 wt % to about 10 wt % of the EPA is a triglyceride conjugate or a diglyceride conjugate; the composition comprises between about 0.1 wt % and about 3.0 wt % mannitol, and the composition does not comprise docosahexaenoic acid (DHA), fatty acid methyl esters or fatty acid ethyl esters, and the composition is suitable for human consumption. It is noted that eicosapentaenoic acid (EPA) refers to cis-5,8,11,14,17-Eicosapentaenoic acid (20:5, n–3) and that docosahexaenoic acid (DHA) refers to cis-4,7,10,13,16,19-Docosahexaenoic acid (22:6(n–3)).

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides a botanical extract comprising an ethanol extract of *Nannochloropsis algae* having between 1 wt % and 20 wt % polar lipids and between 45 wt % and 60 wt % fatty acids, wherein the fatty acids comprise: more than 10 wt % of eicosapentaenoic acid (EPA) as triglyceride conjugates and/or diglyceride conjugates, and less than 15 wt % EPA as free fatty acids.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout. In the accompanying drawings:

FIG. 1 is a high-level schematic illustration of a bioreactor for extracting botanical extracts, according to some embodiments of the invention.

It will be appreciated that for simplicity and clarity of illustration, elements shown in the FIGURES have not necessarily been drawn to scale. For example, the dimensions of some of the elements may be exaggerated relative to other elements for clarity. Further, where considered appropriate, reference numerals may be repeated among the FIGURES to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

U.S. Patent Application Publication Nos. 2019/0345427, 2020/0231925 and 2022/0256884, which are incorporated herein by reference in their entirety, disclose systems and methods of growing algae and of extracting Ω3-rich extracts therefrom.

Embodiments of the present invention provide efficient and economical methods for growing algae and extracting therefrom algal botanical extracts rich in EPA as triglyceride conjugates and/or diglyceride conjugates, and thereby provide improvements to the technological field of Ω3-rich botanical extracts of algae and foods and supplements containing the extracts. Some embodiments provide botanical extracts comprising an ethanol extract of *Nannochloropsis algae* having between 10 wt % and 20 wt % polar lipids and between 45 wt % and 60 wt % fatty acids, wherein the fatty acids comprise more than 10 wt % of eicosapentaenoic acid (EPA) as triglyceride conjugates and/or diglyceride conjugates, and less than 15 wt % EPA as free fatty acids.

EPA level may reach up to 90 wt %, and the botanical extract may be fluid at room temperature. Growth conditions are configured, adjusted and monitored to promote EPA formation in the cell vacuoles, resulting in a high proportion of EPA as tri/di-glyceride conjugates, as well as in a high concentration of 2-3 fatty acids, which merely requires gentle extraction procedures to reach the final products, thereby maintaining the biochemical of the compounds without excessive modifications.

FIG. 1 is a high-level schematic illustration of a bioreactor 100 for extracting botanical extracts 140, according to some embodiments of the invention. Bioreactor 100 comprises one or more tanks filled with water and *Nannochloropsis* algae 90 (e.g., *N. oculata, N. australis, N. gaditana, N. granulate, N. limneitica, N. oceanica, N. salina, Nitzschia paleacea, Phaeodactylum tricornutum, Pavlova lutheri, Rebecca salina*, any strains or combinations thereof, or equivalent algae), and further comprising (i) an illumination system 120 that comprises multiple intense light sources 125, e.g., light emitting diodes (LEDs, e.g., at between 400-700 nm, within sub-ranges thereof, e.g., 400-500 nm, 500-600 nm, 600-700 nm, and/or at specific wavelengths e.g., 650 nm) that may be arranged in one or more horizontal and/or vertical panels (illustrated schematically and only in part) and (ii) a bubbling system 110 associated with a gas supply (e.g., air or nitrogen enriched with $CO_2$, e.g., including a $CO_2$ concentration of 30% or higher), which comprises multiple spargers of at least two types—sparger(s) 110A with large nozzles (e.g., >1 mm in diameter, possibly within a range of 1-5 mm or within subranges thereof) for generating large bubbles 115A that move fast (e.g., 100 $min^{-1}$, indicating the rate of cumulative bubble volume to container volume, possibly within a range of ±30%, of 50-150 $min^{-1}$ or within subranges thereof) through the algae culture and mix it, and sparger(s) 110B with small nozzles (e.g., <1 mm in diameter, possibly within a range of 0.1-1 mm or within subranges thereof) for generating small bubbles 115B that move slowly (e.g., 5 min-, indicating the rate of cumulative bubble volume to container volume, possibly within a range of ±30%, of 2-30 $min^{-1}$ or within subranges thereof) through the algae culture and enable $CO_2$ to diffuse to the algal cells. Possibly more than two types of nozzles may be used to control the mixing of the algae culture and the delivery of $CO_2$ at a sufficient concentration to the algae. The two or more types of spargers (each with multiple nozzles) may be distributed at one or more locations and be configured to generate turbulent mixing of the algae in the cultivation container and provide $CO_2$ to the algae to the extent that maximizes or optimizes their growth and/or their Ω-3 fatty acid content and/or composition, e.g., maximize their EPA (and/or DHA) content and/or association with tri/di-glyceride in the cell vacuoles.

As illustrated schematically in the enlarged region of FIG. 1, the very dense algae culture (e.g., having an algal density of at least 5 g/l, possibly within a range of 5-15 g/l or within subranges thereof) and localized intense light sources 125 create illuminated zones and dark zones within bioreactor 100, and the intense agitation of the algae culture by large bubbles 115B continuously mixes the liquid and moves algal cells 90 between the dark and the illuminated zones. In non-limiting examples, light sources 125 may reach an illumination intensity of any of at least 700 micromole·m$^-$$_2$s$^{-1}$, at least 1000 micromole·m$^{-2}$s$^{-1}$, at least 1200 micromole·m$^{-2}$s, or intermediate values each, e.g., using at least 24 LEDs over an area of 4 m$^2$ with a light path of about 2.5 cm—defining the reach of the illuminated zones). The intense non-homogenous illumination, dark zone periods, and high level of $CO_2$ fed to algal cells 90 by small bubbles 115A yield a high growth rate of the algae, and was also found to modify the biosynthetic pathways employed by the algae to form organic compound. For example, at high density conditions, the illuminated zones may extend to a few millimeters (e.g., 1-5 mm) from point sources 125, while the dark zones between the illuminated zones may extend over a few tens of millimeter (e.g., 20-30 mm) between consecutive illuminated zones—so that individual algae cells spend periods in dark zones to assimilate $CO_2$ using the light energy absorbed in the illuminated zones.

The growing conditions may be monitored to maintain optimal growth, e.g., the temperature may be kept constant (e.g., at any of 15° C., 20° C., 25° C., 27° C., between any of 12-17° C., 15-20° C., 20-25° C., 25-30° C., 20-40° C., 20-50° C. or within subranges thereof) or be allowed to change within a specified range, chemical conditions such as the pH, $O_2$ and $CO_2$ content and/or content of various ions or compounds may be kept constant or be allowed to change within a specified range (e.g., between pH values of 6.7 and 7.2, or any subranges thereof). For example, the organic carbon content may be maintained at or around 20 wt %. Alternatively or complementarily, $CO_2$ concentration may be kept at or below 40% and/or the pH may be monitored to indicate and regulate the $CO_2$ concentration. Algae density may likewise be kept constant or be allowed to change within a specified range. The flow rates of small bubbles 115B from sparger(s) 110B with the small nozzles may be adjusted to increase or reduce $CO_2$ levels (e.g., increased above 5 $min^{-1}$, e.g., to 7-10 $min^{-1}$ to increase $CO_2$ levels, or reduced to 2 $min^{-1}$ to reduce $CO_2$ levels). In certain embodiments, the level of various nutrients may be monitored, and additional nutrients may be provided via one or both bubble streams, e.g., phosphorous may be added to the gas supply if a low P level is detected or if growth is inhibited.

In particular, the inventors have surprisingly found that these growth conditions cause the algae to form more EPA in the cell vacuoles (in form of triglyceride conjugates and/or diglyceride conjugates) and less EPA in the cell membranes (in form of polar lipids). Moreover, the intense growing conditions also yielded a relatively high concentration of EPA in the algal biomass.

Algal slurry is periodically or continuously removed from bioreactor 100 (e.g., to balance the growth of biomass), mixed with ethanol (stage 130) and botanical extract 140 is extracted therefrom by phase separation (stage 132) and thermal separation(s) (stage 134), of one or more of the separated phases. Non-limiting examples for parameters of the separation process include a volume ratio of at least 5:1 (or possible within the range 3.5:1 to 7:1 or intermediate subranges) between ethanol and the algal slurry (the mixture may be stirred for between 0.5-4 hours, e.g., for 2 hours), use of centrifugation for the phase separation, possibly under vacuum (e.g., under a pressure between 75-125 mbar) and a temperature range of between 55° C.-65° C. for the thermal separation, which, due to the initial high concentration of 2-3 fatty acid such as EPA, may be sufficient to reach the required concentration while minimizing thermal and chemical modifications of the botanical extract. Botanical extract 140 thus reaches a concentration of between 10 wt % and 2 0 wt % polar lipids and between 45 wt % and 6 5 wt % fatty acids. In certain embodiments, up to 90% of the algal mass may be removed per day. In certain embodiments, the yield from bioreactor 100 may reach 2.8 gr/l providing a 2-3 fatty acids yield of 190 mg/l per day.

In certain embodiments, botanical extract 140 reaches a concentration of between 10 wt % and 50 wt % polar lipids (e.g., glycolipids and phospholipids) and between 15 wt % and 90 wt % EPA, which may be split into 3-25 wt % phospholipids, 3-25 wt % glycolipids, and 15-35 wt % (non-polar) tri/di-glycerides. It is noted that the consistency and the very dark color of botanical extract 140 limit the analysis of its constituent by common profiling methods such as optical and spectroscopical methods as well as gas chromatography-mass spectrometry (GC-MS).

In particular, the inventors have surprisingly found that extract 140 yielded by separation stages 132, 134 is already highly concentrated (due to the special growing conditions) and does not require further purification and isolation of EPA to reach higher EPA concentration. Accordingly, botanical extract 140 is kept from in its relatively pristine form, avoiding high temperatures and chemical modification. Moreover, due to the different allocation of EPA within the algal cells, resulting botanical extract 140 comprises more than 10 wt % of EPA as triglyceride conjugates and/or diglyceride conjugates (due to higher EPA concentration in the cell vacuoles) and less than 15 wt % EPA as free fatty acids (due to lower concentration of EPA in polar lipids of the cell membranes). In certain embodiments, botanical extract 140 comprises more than 15 wt % of EPA as triglyceride conjugates and/or diglyceride conjugates and less than 10 wt % EPA as free fatty acids. In certain embodiments, botanical extract 140 comprises about 18 wt % of EPA as triglyceride conjugates and/or diglyceride conjugates and about 7 wt % EPA as free fatty acids.

In certain embodiments, resulting botanical extract 140 comprises more than 10 wt % of EPA and/or DHA as triglyceride conjugates and/or diglyceride conjugates (due to higher EPA and/or DHA concentration in the cell vacuoles) and less than 15 wt % EPA and/or DHA as free fatty acids (due to lower concentration of EPA and/or DHA in polar lipids of the cell membranes). In certain embodiments, botanical extract 140 comprises more than 15 wt % of EPA and/or DHA as triglyceride conjugates and/or diglyceride conjugates and less than 10 wt % EPA and/or DHA as free fatty acids. In certain embodiments, botanical extract 140 comprises about 18 wt % of EPA and/or DHA as triglyceride conjugates and/or diglyceride conjugates and about 7 wt % EPA and/or DHA as free fatty acids.

Various embodiments comprise food products and/or nutritional supplements that comprise botanical extracts 140. In certain embodiments, food products and/or nutritional supplements that comprise botanical extracts 140 may be used to support anti-depression treatment and/or cholesterol management.

Advantageously, compared to prior art such as U.S. Pat. Nos. 9,629,820, 10,123,986 and 10,039,734, and U.S. Patent Application Publication No. 20140179781 which cultivate the algae in an open pond system and consequentially produce different compositions, some of the disclosed embodiments provide EPA compositions having between 15 wt % and 9 0 wt % of EPA and between 10 wt % and 50 wt % of polar lipids, wherein: the polar lipids comprise phospholipid-conjugates and glycolipid-conjugates; between 3 wt % and 25 wt % of the EPA in the composition is a phospholipid-conjugate; between 3 wt % and 25 wt % of the EPA in the composition is a glycolipid-conjugate; between 15 wt % and 35 wt % of the EPA in the composition is a triglyceride-conjugate or a diglyceride-conjugate. In some embodiments, less than 10 wt % of the EPA in the composition is in free fatty acid form. In some embodiments, the EPA composition does not comprise docosahexaenoic acid (DHA) and is suitable for human consumption.

For example, Table 1 presents a non-limiting example of a biomass analysis used to extract disclosed compositions. Table 1 presents, on an ash-free-dry-weight (AFDW) basis, the EPA concentration, the concentration of polar lipids (including glycolipids and phospholipid) and the concentration of non-polar lipid (tri- and di-glycerides). The data is derived from analysis of 25 batches over a period of about 3 years and compared to biomass analysis of N. oculata grown in open ponds (as taught by, e.g., U.S. Patent Application Publication No. 20140179781).

TABLE 1

Composition analysis of N. oculata biomass (controlled growth) compared with prior art (open pond) compositions. Data in wt %.

| Biomass grown as disclosed | EPA | Polar lipids | | | Triglycerides (Non-Polar lipids) |
|---|---|---|---|---|---|
| | | Phospholipids | Glycolipids | Total | |
| Minimum | 10.2 | 1.8 | 3.2 | 5.0 | 25.0 |
| Maximum | 9.2 | 3.5 | 5.6 | 9.1 | 32.0 |
| Average | 9.7 | 2.8 | 4.5 | 7.3 | 28.5 |
| Standard deviation | 0.5 | 0.8 | 0.9 | 1.7 | 3.7 |
| Prior art biomass | <5.4 | | | | <15 |

For example, compared with the prior art biomass of Nannocloropsis oculata cultivated in an open pond system, algal biomass grown under controlled conditions disclosed herein has a double average EPA content (9.7 wt % versus 5.4 wt %), and a double average triglyceride (non-polar) content (28.5 wt % versus 15 wt %). Disclosed botanical extracts 140 derived from an aqueous ethanolic extraction of the biomass was between 39-53% of the algal AFDW biomass, with an EPA yield of >90%. Taking into account the % extractables and yield, the data demonstrate that the EPA concentration in the extract (which corresponds to the algal biomass composition) is higher than 15 wt %, the concentration of the polar lipids (glycolipids and phospholipids) is higher than 13 wt %, the concentration of triglycerides is higher than 50 wt % (e.g., 59 wt %), and the concentration of EPA-triglyceride-conjugates is higher than 15 wt % (e.g., 28 wt %)—all in contrast to the prior art such as U.S. Patent Application Publication No. 20140179781). An additional difference is that disclosed extracts have an unusually low free fatty acid composition, below <10 wt % (e.g., 7 wt %).

In another example, Table 2 presents a non-limiting example of an analysis of EPA in triglyceride and free fatty acid forms in disclosed extract compositions.

TABLE 2

NMR analysis of the form of EPA in the extracts (%).

| EP A form (NMR peak): | Free fatty acid (177.8 ppm) | Triglycerides | | |
|---|---|---|---|---|
| | | Total | SN1/3 (173.4 ppm) | SN2 (173 ppm) |
| Sample 1 | 4.9 | 18.7 | 13.6 | 5.1 |
| Sample 2 | 4.8 | 18.5 | 13.7 | 4.8 |
| Sample 3 | 4.2 | 18.7 | 13.7 | 5.0 |

As illustrated Table 2, a low proportion (under 5 wt %) of the EPA is found in free fatty acid form (FFA) in the disclosed extracts, while a large portion of the EPA (over 15 wt %) is in triglyceride forms (SN2 denoting a central position of the EPA on the glycerol backbone, while SN1/3 denotes an end position of the EPA on the glycerol backbone)—distinguishing disclosed extracts from prior art extracts.

Additionally, while prior art extracts have the consistency of wax and cannot be handled at temperatures under 90° C. (see U.S. Patent Application Publication No. 20140179781), possibly due to their high level of polar lipids and free fatty acids and low level of glyceride lipid conjugates, disclosed extracts 140 are typically liquid or semi-liquid at about 40° C., possibly due to their lower level of free fatty acids and higher level of glyceride-lipid-conjugates. In certain embodiments, botanical extract 140 has different rheological characteristics than prior art extracts such as disclosed in U.S. Pat. Nos. 9,629,820, 10,123,986 and 10,039,734, and U.S. Patent Application Publication No. 20140179781, in particular better flow characteristics, possibly due to the different growth conditions and extraction conditions that result in different extract component that improve the flowability of extracts 140. For example, the different growth and extraction conditions may have yielded a different profile of algal polysaccharide, which includes a larger part of ethanol-soluble polysaccharide (e.g., algaenan, e.g., Scholz et al. 2014, Ultrastructure and composition of the *Nannochloropsis gaditana* cell wall, Eukaryotic Cell 13(11): 1450-1464) that make botanical extracts 140 more fluid (see, e.g., Bernaerts 2019, The role of structural biopolymers in the functionalization of microalgae for food processing. Dissertation, KU Leuven, Belgium, Zailer 2019, Holistic control of fats and oils by NMR spectroscopy, Encyclopedia of Food Chemistry, vol. 2, 168-181 and Audo et al. 2012, Relationship between microalgae lipid extracts composition and rheological properties, 2nd International Symposium on Asphalt Pavements et Environnement, Transportation Research Board, of The National Academies, France). The inventors suggest that the growth and extraction conditions disclosed herein provide extracts 140 with modified and improved rheological characteristics with respect to the prior art, e.g., by modifying the profile of algal polysaccharides.

It is noted that bioreactor 100 is described above briefly, and may further comprise additional pipework and valves, pumping and filtering elements, as well as control, sensing and regulatory elements for regulating material flow (e.g., water, gas, slurry as well as the extraction process), which are described, e.g., in WIPO Publications Nos. 2018134818, 2018134819, 2018134820, 2018154565 and 2020240551, which are incorporated herein by reference in their entirety. It is further noted that a value modified by the term "about" is understood to encompass ±10% of the value.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A food product or a nutritional supplement comprising an EPA (eicosapentaenoic acid) composition, the EPA composition comprising between 15 wt % and 90 wt % of EPA and between 10 wt % and 50 wt % of polar lipids, wherein:
    the polar lipids comprise phospholipid-conjugates and glycolipid-conjugates;
    between 3 wt % and 25 wt % of the EPA in the composition is a phospholipid-conjugate;
    between 3 wt % and 25 wt % of the EPA in the composition is a glycolipid-conjugate;
    between 15 wt % and 35 wt % of the EPA in the composition is a triglyceride-conjugate or a diglyceride-conjugate; and
    the EPA composition does not comprise docosahexaenoic acid (DHA) and is suitable for human consumption.

2. The food product or nutritional supplement of claim 1, wherein less than 10 wt % of the EPA in the composition is in free fatty acid form.

3. A food product or a nutritional supplement comprising a botanical extract, the botanical extract comprising an ethanol extract of *Nannochloropsis* algae having between 10 wt % and 50 wt % polar lipids and between 45 wt % and 60 wt % fatty acids, wherein the fatty acids comprise:
    more than 10 wt % of eicosapentaenoic acid (EPA) as triglyceride conjugates and/or diglyceride conjugates, and
    less than 15 wt % EPA as free fatty acids.

4. The food product or nutritional supplement of claim 3, wherein the fatty acids comprise more than 15 wt % EPA as triglyceride conjugates and/or diglyceride conjugates and less than 10 wt % EPA as free fatty acids.

5. The food product or nutritional supplement of claim 3, wherein the fatty acids comprise 18 wt % EPA as triglyceride conjugates and/or diglyceride conjugates and 7 wt % EPA as free fatty acids.

6. The food product or nutritional supplement of claim 4, wherein the *Nannochloropsis algae* comprise *N. oculata*.

7. The food product or nutritional supplement of claim 3, wherein the *Nannochloropsis algae* are grown at high density of at least 5 g/l, under high illumination intensity of at least 700 micromole $m^{-2}s^{-1}$, and undergoing continuous bubbling and $CO_2$ enrichment.

8. A food product or a nutritional supplement comprising a botanical extract, the botanical extract comprising an ethanol extract of *Nannochloropsis algae* having between 10 wt % and 50 wt % polar lipids and between 45 wt % and 60 wt % fatty acids, wherein the fatty acids comprise:

more than 10 wt % of eicosapentaenoic acid (EPA) and/or docosahexaenoic acid (DHA) as triglyceride conjugates and/or diglyceride conjugates, and less than 15 wt % EPA and/or DHA as free fatty acids.

9. The food product or nutritional supplement of claim 8, wherein the fatty acids comprise more than 15 wt % EPA and/or DHA as triglyceride conjugates and/or diglyceride conjugates and less than 10 wt % EPA and/or DHA as free fatty acids.

10. The food product or nutritional supplement of claim 8, wherein the fatty acids comprise 18 wt % EPA and/or DHA as triglyceride conjugates and/or diglyceride conjugates and 7 wt % EPA and/or DHA as free fatty acids.

11. The food product or nutritional supplement of claim 8, wherein the *Nannochloropsis algae* comprise *N. oculata*.

12. The food product or nutritional supplement of claim 8, wherein the *Nannochloropsis algae* are grown at high density of at least 5 g/l, under high illumination intensity of at least 700 micromole $m^{-2}s^{-1}$, and undergoing continuous bubbling and $CO_2$ enrichment.

\* \* \* \* \*